US00PP21383P3

(12) United States Plant Patent
Bodiford

(10) Patent No.: US PP21,383 P3
(45) Date of Patent: Oct. 12, 2010

(54) ***HIBISCUS* PLANT NAMED 'ALMA'S STAR'**

(50) Latin Name: *Hibiscus mutabilis almanii*
Varietal Denomination: Alma's Star

(76) Inventor: Alma N. Bodiford, 654 Springhill Rd., Luverne, AL (US) 36049

( * ) Notice: Subject to any disclaimer, the term of this patent is extended or adjusted under 35 U.S.C. 154(b) by 345 days.

(21) Appl. No.: 11/974,300

(22) Filed: Oct. 12, 2007

(65) Prior Publication Data

US 2009/0183289 P1 Jul. 16, 2009

(51) Int. Cl.
*A01H 5/00* (2006.01)

(52) U.S. Cl. ..... Plt./257

(58) Field of Classification Search ..... Plt./257

See application file for complete search history.

*Primary Examiner*—Kent L Bell
(74) *Attorney, Agent, or Firm*—Novak Druce + Quigg LLP

(57) ABSTRACT

A new and distinct cultivar of *Hibiscus* named 'Alma's Star' particularly characterized by its unique and distinct bloom.

4 Drawing Sheets

Botanical classification: *Hibiscus mutabilis almanii* 'Alma's Star'.

Varietal denomination: 'Alma's Star'.

BACKGROUND OF THE INVENTION

1. Field of the Invention

The present invention relates to a new and distinct cultivar of *Hibiscus* plant, botanically known as *Hibiscus mutabilis,* and hereinafter referred to by the cultivar name 'Alma's Star'.

2. Background

The genus *Hibiscus* is a wide one, comprising some 150 to 160 species, which occur mainly in tropical and sub-tropical regions. *Hibiscus mutabilis,* commonly known as Confederate rose, cotton rose, Dixie rose mallow and Tree lotus, is a native of China, introduced to North America in the 18$^{th}$ century, and has been thriving in the southern landscapes for many generations.

*Hibiscus mutabilis* is a perennial or shrub *Hibiscus* better known as the Confederate rose. It tends to be shrubby or treelike, though it behaves more like a perennial in northern zones. Flowers are double and are 4 to 6 inches in diameter; they open white or pink, and change to deep red. Propagation by cuttings root easiest in early spring, but cuttings can be taken at almost any time. When it does not freeze, the Confederate rose can reach heights of 12 to 15 feet with a woody trunk; however, a multi-trunk bush 6 to 8 feet tall is more typical. Once a very common plant throughout the South, Confederate rose is an interesting and attractive plant that grows in full sun or partial shade, and prefers rich, well-drained soil.

SUMMARY OF THE INVENTION

The following represent the distinguishing characteristics of the new *Hibiscus* cultivar 'Alma's Star'. The distinguishing feature of 'Alma's Star' is its unusual bloom. 'Alma's Star' exhibits buds of unusual size at the tips of its flowering stalks. These buds open up to present a flower that is a bundle of five distinct flowers, four outer and a central cluster that produce a bundle similar to a quartered rose.

BRIEF DESCRIPTION OF THE DRAWING

The accompanying colored photographs illustrate the overall appearance of the new cultivar, showing the colors as true as it is reasonably possible to obtain in colored reproductions of this type.

BOTANICAL DESCRIPTION OF THE PLANT

Figure 1:
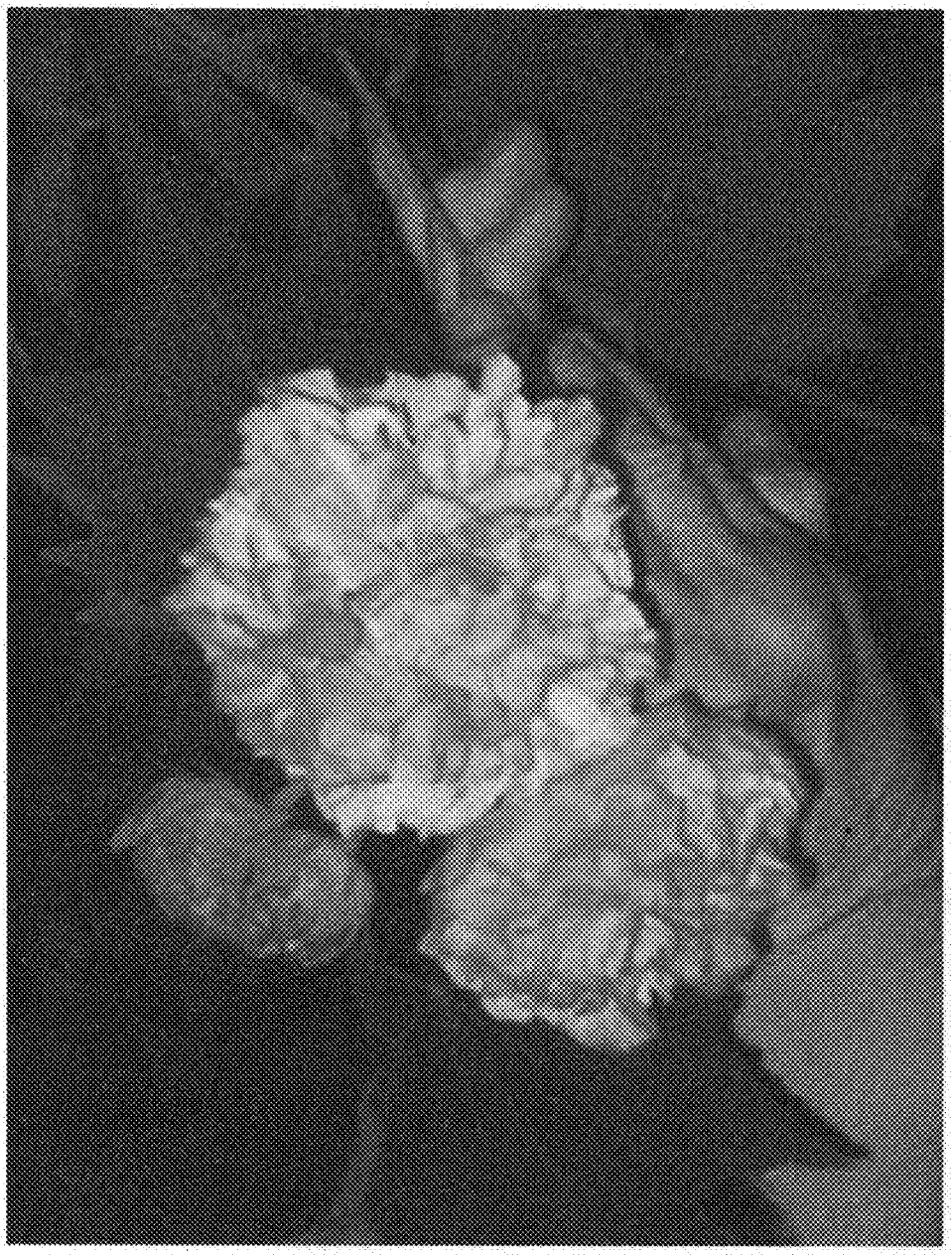
FIG. 1 depicts the distinctive blooms and buds of the 'Alma's Star'. In the foreground is a close-up view of the upper surface of a fully expanded bloom (light pink in color) and a side perspective view of a second bloom (darker pink in color) of 'Alma's Star'. The close-up view shows the centers (yellow coloration) of two of the five individual blooms that make up each bloom of 'Alma's Star'. Visible in the background are two buds of unusual size. Bloom colors in the photographs may appear different from the actual colors due to light reflectance.
Figure 2:
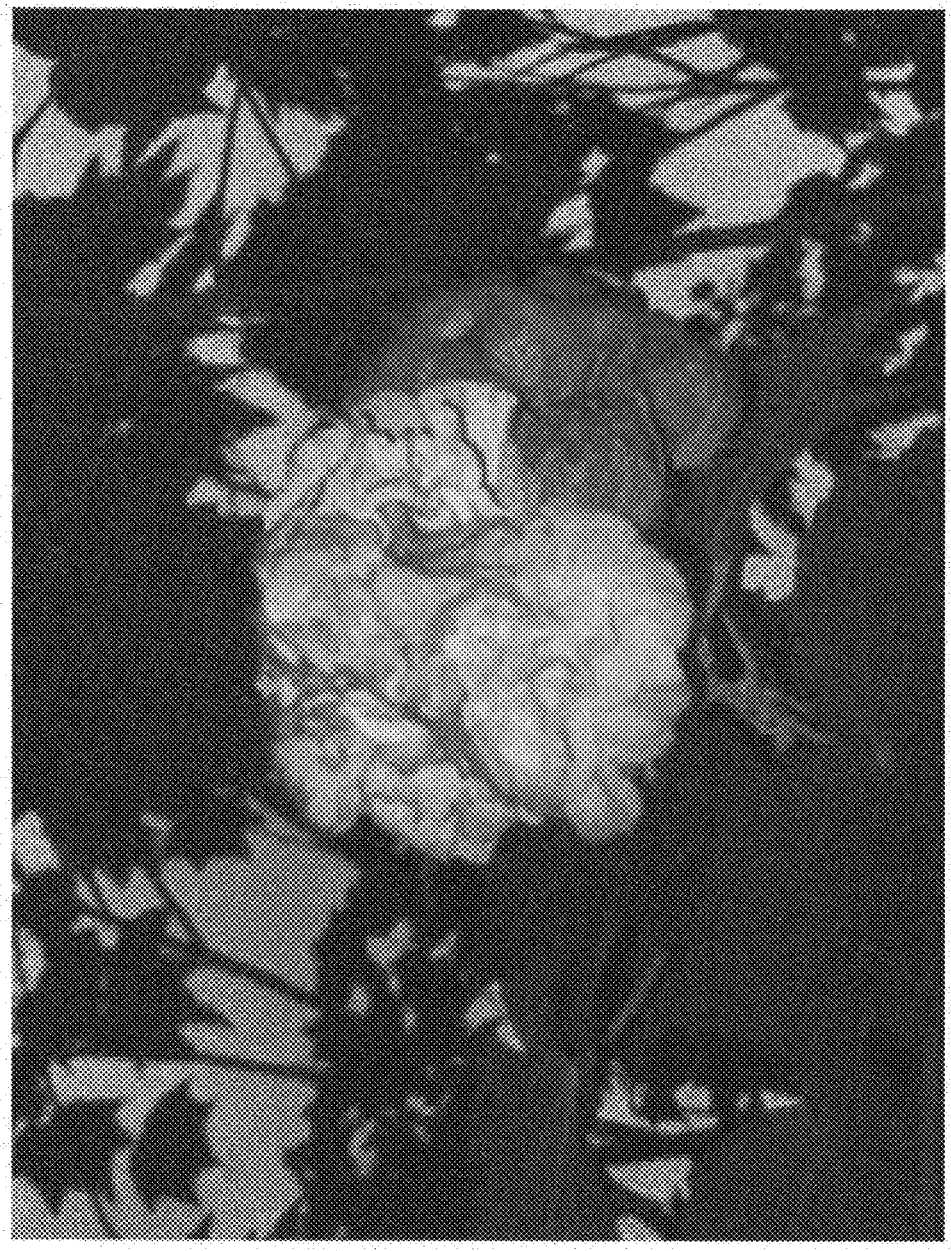
FIG. 2 shows another view of blooms of 'Alma's Star' on a single flowering stalk. The centers (yellow coloration) of three of the five individual blooms that make up each bloom of 'Alma's Star' are distinctly visible. Bloom colors in the photographs may appear different from the actual colors due to light reflectance.
Figure 3:
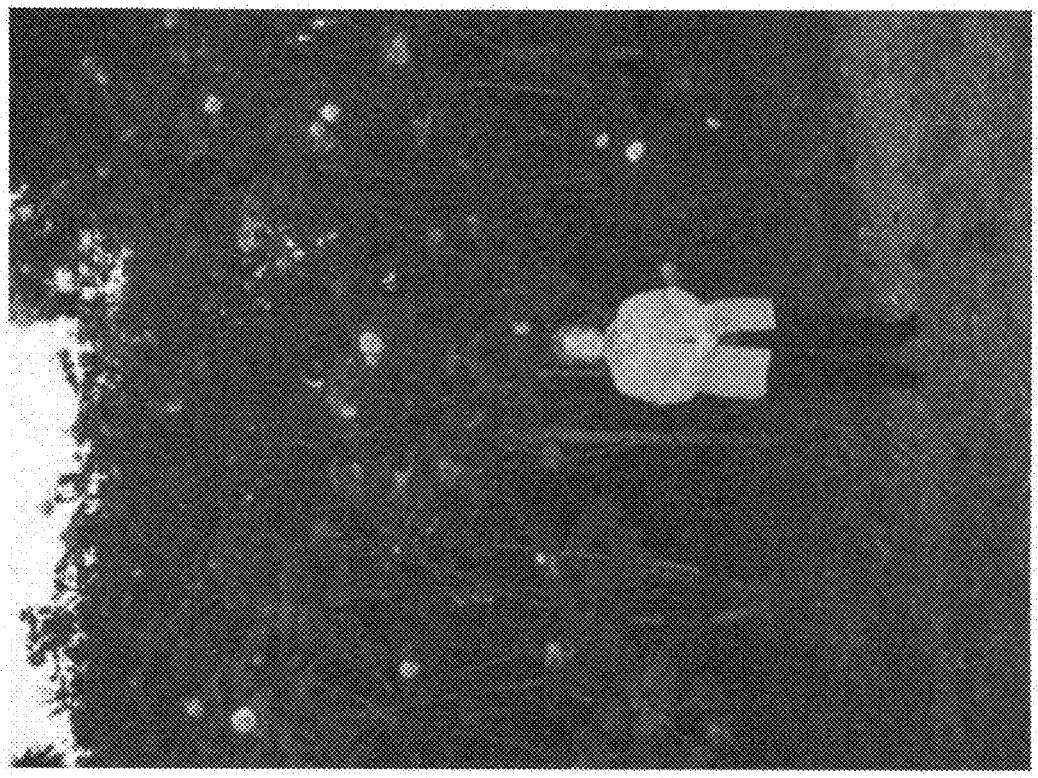
FIG. 3 shows full grown plants of 'Alma's Star'.
Figure 4:
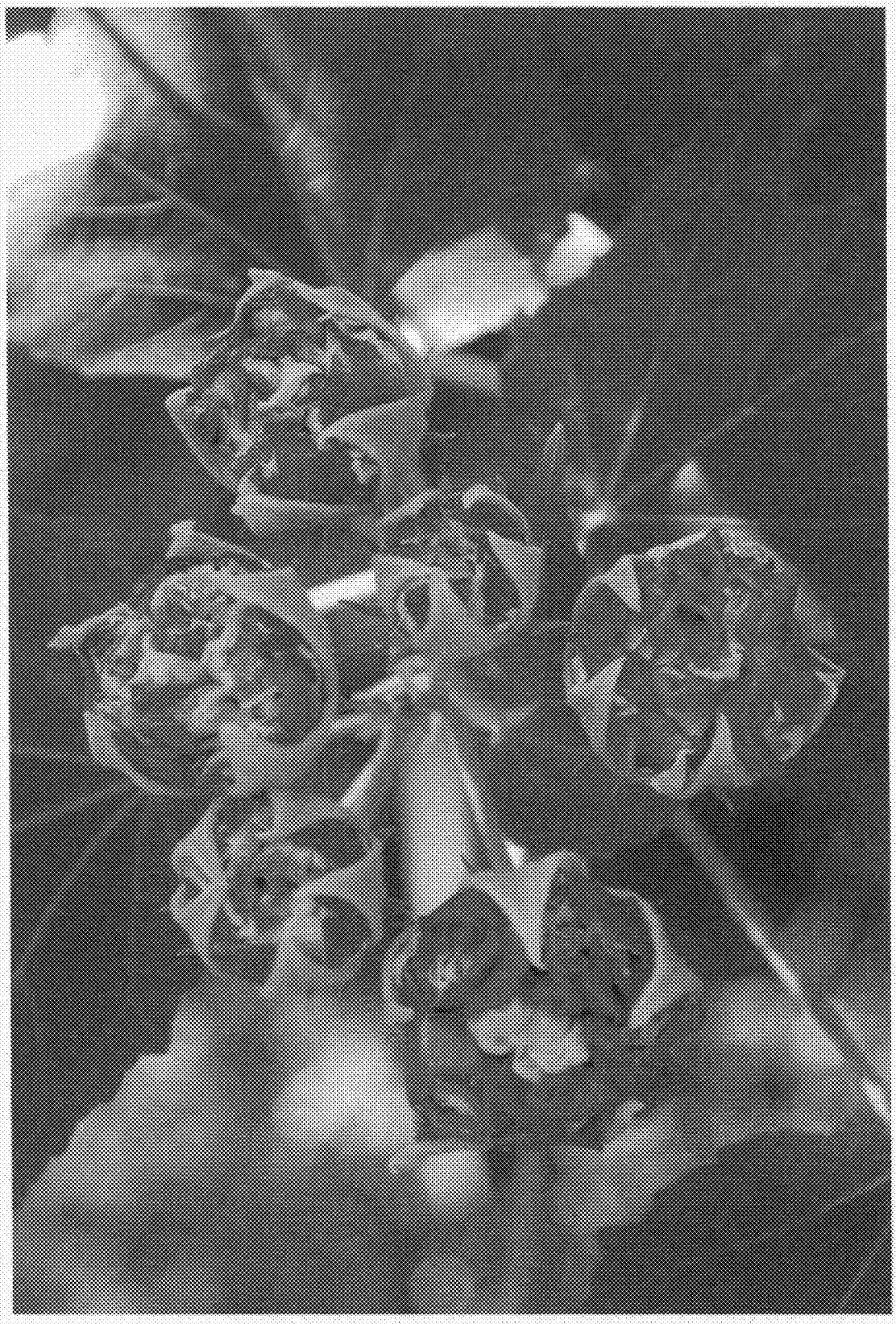
FIG. 4 shows buds of 'Alma's Star'.

The new cultivar is a product of an effort by the inventor to propagate garden variety *Hibiscus mutabilis,* in Alabama, United States of America. The objective was to restock the garden with new plants without going through seed harvesting. The new cultivar developed when natural root graftings, of rooted stalk cuttings from a Rose mallow *Hibiscus moscheutos* and a Confederate rose, *Hibiscus mutabilis,* were planted together. Two mutated "sports" (mutated sprouts) appeared and produced unique pink flowers, each containing four or five small and separate flowers, which were sterile and produced no viable seed. The new cultivar, 'Alma's Star', was discovered and selected by the inventor in 1997 in a cultivated area in Ala., United States of America. Asexual reproduction of the new cultivar, by top cuttings, stem cuttings and divisions in Alabama, United States of America, has shown that the unique features of this new *Hibiscus* cultivar are stable and reproduced true to type in successive generations.

The new cultivar has not been observed under all possible environmental conditions. The phenotype may vary somewhat with variations in environment such as temperature, light intensity and fertilizer rate, without, however, any variance in genotype.

The following traits have been repeatedly observed and are determined to be the unique characteristics of 'Alma's Star'. These characteristics in combination distinguish 'Alma's Star' as a new and distinct cultivar: Plants of the new *Hibiscus* have a unique and distinct bloom. The new cultivar produces buds of unusual size at the tips of its flowering stalks. These buds open up to present a flower that is a bundle of five distinct flowers, four outer and a central cluster that produced a bundle similar to a quartered rose. Plants of the new *Hibiscus* grow at a faster rate than the class of confederate rose and are compact in growth habit. The new cultivar produces divisions readily giving plants a full and dense appearance. Root development on the cuttings is rapid. Typically roots are observed at 4-5 weeks in water with no additives. Roots are initiated in plain water in a well-lit area in a clear vessel. Roots on cuttings can be developed year round. Plants of the new *Hibiscus* have good postproduction longevity and are tolerant of low light conditions. However, best growth is in full sun. Plants of the new *Hibiscus* are tolerant of low winter temperatures, with the stalks surviving temperatures as low as 22 degrees Fahrenheit. Typically, the only cold injury observed is loss of leaves at hard frost. Additionally, the new cultivar is exceptionally resistant to diseases common to *Hibiscus*.

The following observations, measurements and comparisons describe plants grown in Luveme, Ala., Unites States of America, and conditions which closely approximate those used in horticultural practice. At the time of the following observations, measurements, and comparisions, the plants were approximately 5 to 6 years old. Plants were grown under day temperatures ranging from 60 degree to 105 degree Fahrenheit and night temperatures ranging from 22 degree to 75 degree Fahrenheit.

In the following description, color references are made to The Royal Horticultural Society Colour Chart (R.H.S. Colour Chart) except where general terms of ordinary dictionary significance are used. Botanically, the new cultivar is classified as *Hibiscus mutabilis almanii* 'Alma's Star'.

'Alma's Star' is a naturally occurring whole plant mutation of *Hibiscus mutabilis*. The new cultivar is propagated by stalk or root cutting. Roots can be initiated year round. Typically time to initiate roots is 4-5 weeks. Roots are initiated in a well-lit area, in water with no additives and a clear vessel. The new cultivar tends to have deep roots with the roots being similar in appearance to those of the class of Confederate rose.

'Alma's Star' grows in a day temperature range of 60 degrees to 105 degrees Fahrenheit. The new plant is tolerant of low temperatures. Apart from loss of leaves, which occurs on exposure to hard frost, the stalks survive in temperatures as low as 22 degrees Fahrenheit.

The new cultivar grows upright, multi-stemmed, outward spreading with an inverted triangle, symmetrical appearance. Numerous divisions give plants a very full, dense appearance. A typical 3 gallon plant has about 8 to 10 lateral branches per plant. The lateral branch length is from about 2 to 3 feet. The lateral branch diameter is about 0.5 to 0.75 inches. The internode length is from about 2 to 3 inches. The texture is medium. The color of the lateral branches are RHS Colour Chart Fan #3 Yellow Green Group #144A. The new cultivar appears tall to medium, bushy, well branched and woody. It has the ability to reach a height of 20 feet from soil surface to top of leaf canopy and forms a 12 feet spread, with a rounding habit. It is tolerant of low-light but grows best in full sun. The new cultivar has a vigorous, rapid growth rate. Plants will form within 30-45 days of planting a rooted top cutting.

The new cultivar has a dense to medium foliage with leaves that are medium to large in size. The leaf color varies between light and dark green in color. The leaves are deeply lobed with 5 lobes, undulating with serrated margins and hairy on the undersides. The leaves are smooth on the top sides. Leaf length, fully expanded, is about 9.5 inches and width is about 10 inches for a mature leaf. Leaf length of a medium age leaf in about 6 inches and width is about 6 inches. There is an alternating leaf arrangement on the branches. The leaf color is RHS Colour Chart Fan #3 Green Group #137A. There are 6 veins fanning from and protruding from the base of the leaf and the color on both surfaces is RHS Colour Chart Fan #3 Yellow Green Group #144A. The apex comes to a pointed tip with 5 lobes with a central pointed tip and the color is RHS Colour Chart Fan #3 Green Group #137A.

The petiole is about 5.5 to 7 inches long with a diameter of about 0.125 to 0.1875 inches. The color of the petiole is RHS Colour Chart #3 Yellow Green Group #144A.

Blooms of the new cultivar are of a medium texture with partial overlapping petals. The new cultivar exhibits buds of unusual size at the tips of its flowering stalks. The buds are round in shape with a length of about 1.25 to 2 inches and a diameter of about 1.25 to 2 inches. The color of the buds is RHS Colour Chart Fan #2 Red Purple Group #57 A. These buds open up to present a flower that is a bundle of five distinct flowers, four outer and a central cluster. The bundle is similar to a quartered rose. The flower bundle is about 4 to 5 inches deep and about 4 to 7 inches in diameter. Each distinct flower is about 4 to 5 inches deep and about 2.5 to 3 inches in diameter. There are about 3 to 6 flower bundles per lateral branch. The bloom holds color and is sterile. The new cultivar blooms best from summer to autumn. The individual blooms last approximately one week on the plant. The bloom is a range of the colors at RHS Colour Chart Fan #2 Red-Purple Group #57 A, B, C, and D. The base petals of the bloom are pink to rosy in color. The edges of the petals are pink tinged with white. The halo is bright pink to rosy. There are approximately 240 petals in an average bloom. The petals are shorter near the center and taller towards the outside of the flower. The petal form is ruffled, satiny in texture and reflexed or overlapped. The petals are fan-shaped with a length of about 1.5 inches and a width of about 2.25 inches. The apex is smooth and the margin is wavy. The petals are a range of the colors at RHS Colour Chart Fan #2 Red-Purple Group #57 A, B, C, D. The petal texture is generally smooth on the upper and lower surfaces with veins that are more pronounced on the lower surface. The center is compact and hidden. The petals have no discernable spots or splotches. There is no style or stigmas evident. The blooms present a tinge of white streaks. The blooms bear no fragrance. The base has 5 sepals equally spaced around the base of the flower. The sepal is triangular in shape. The length of the sepal is about 1.75 inches and the width is about 0.75 inches. The apex of the sepal is pointed with veins and the margin is smooth. The sepal is hairy on both surfaces. The color of the sepal is RHS Colour Chart #3 Yellow Green Group #144A. The spread of the five sepals at the widest point is about 3.5 inches. There are about 8 to 10 epicalyx per flower. Each epicalyx is swordshaped and about 0.125 inches wide. The texture is hairy on both surfaces. The color of the epicalyx is RHS Colour Chart Fan #3 Yellow Group #144A and no veins are visible. The peduncle is about 0.75 inches in length and about 0.125 inches in diameter. The peduncle of the flower stalk is about 1.75 inches long. The texture of the peduncle is smooth and the color is RHS Colour Chart Fan #3 Yellow Group #144A. Plants of the new cultivar are exceptionally resistant to diseases common to *Hibiscus* and no less tolerant to pests than other hardy *Hibiscus* plants.

The invention claimed is:

1. A new and distinct variety of *Hibisus mutabilis* plant named 'Alma's Star' as described and illustrated.

* * * * *